(12) United States Patent
Gannabathula et al.

(10) Patent No.: US 9,539,289 B2
(45) Date of Patent: Jan. 10, 2017

(54) IMMUNOSTIMULATORY COMPOSITIONS AND METHODS OF MANUFACTURE

(71) Applicant: APIMED MEDICAL HONEY LIMITED, Paengaroa (NZ)

(72) Inventors: Swapna Gannabathula, Auckland (NZ); Geoff Krissansen, Auckland (NZ); Jonathan McDonald Counsell Stephens, Tuakau (NZ); Gregor Aaron Steinhorn, Auckland (NZ)

(73) Assignee: APIMED MEDICAL HONEY LIMITED, Paengaroa (NZ)

( * ) Notice: Subject to any disclaimer, the term of this patent is extended or adjusted under 35 U.S.C. 154(b) by 0 days.

(21) Appl. No.: 14/394,966

(22) PCT Filed: Apr. 17, 2013

(86) PCT No.: PCT/NZ2013/000070
§ 371 (c)(1),
(2) Date: Oct. 16, 2014

(87) PCT Pub. No.: WO2013/157961
PCT Pub. Date: Oct. 24, 2013

(65) Prior Publication Data
US 2015/0071968 A1  Mar. 12, 2015

(30) Foreign Application Priority Data

Apr. 17, 2012  (NZ) ........................................ 599435

(51) Int. Cl.
| | | |
|---|---|---|
| *A61K 9/00* | (2006.01) | |
| *A61K 35/64* | (2015.01) | |
| *A61K 35/644* | (2015.01) | |
| *A61K 38/16* | (2006.01) | |
| *A61K 31/715* | (2006.01) | |
| *A61K 38/17* | (2006.01) | |

(52) U.S. Cl.
CPC ........... *A61K 35/644* (2013.01); *A61K 31/715* (2013.01); *A61K 38/16* (2013.01); *A61K 38/1767* (2013.01)

(58) Field of Classification Search
CPC .................................................. A61K 35/644
USPC .......................................................... 424/725
See application file for complete search history.

(56) References Cited

U.S. PATENT DOCUMENTS

| | | |
|---|---|---|
| 6,956,144 B2 | 10/2005 | Molan |
| 7,714,183 B2 | 5/2010 | Caskey |
| 8,568,790 B2 | 10/2013 | Moloney |
| 8,632,810 B2 | 1/2014 | Moloney |
| 8,815,298 B2 | 8/2014 | Moloney |
| 2008/0305995 A1 | 12/2008 | Suzuki et al. |

FOREIGN PATENT DOCUMENTS

WO   WO-2011/139168 A1   11/2011

OTHER PUBLICATIONS

Gannabathula et al., Journal of Investigative Dermatology, Sep. 2012, vol. 132, Suppl. 2, pp. S116, Abstract No. 667. Meeting Info: 42 annual Meeting of the European Society for Dermatological Research, ESDR 2012, Venice, Italy, Sep. 19, 2012-Sep. 22, 2012.*
Bilikova et al., "Apisimin, a new serine-valine-rich peptide from honeybee (*Apis mellifera* L.) royal jelly: purification and molecular characterization," FEBS Lett (2002) 528(1-3):125-129.
Gannabathula et al., "Arabinogalactan proteins contribute to the immunostimulatory properties of New Zealand honeys," Immunopharmacol Immunotoxicol (2012) 34(4):598-607.
International Search Report for PCT/NZ2013/000070, mailed Aug. 13, 2013, 4 pages.
Written Opinion for PCT/NZ2013/000070, dated Aug. 13, 2013, 4 pages.

* cited by examiner

*Primary Examiner* — Maryam Monshipouri
(74) *Attorney, Agent, or Firm* — Morrison & Foerster LLP (57) ABSTRACT

Immune-stimulatory compositions and methods of manufacture are described with an unexpectedly greater immunostimulatory effect on the immune system than the individual components alone. The compositions include a combination of arabinogalactan protein (AGP) compounds, particularly those derived from honey or with similar activity to honey derived AGP's along with apisimin proteins, peptides or functional fragments thereof, particularly those isolated from royal jelly or apisimin produced via recombinant methods.

16 Claims, 5 Drawing Sheets

| 1 | Apisimin |
| 2 | Insulin |
| 3 | Bovine albumin |

SEQUENCE LISTING

```
<160> NUMBER OF SEQ ID NOS: 1

<210> SEQ ID NO 1
<211> LENGTH: 382
<212> TYPE: DNA
<213> ORGANISM: Apis mellifera

<400> SEQUENCE: 1
gcacgaggaa ccgagctttc taaaagcaat tccaaacagc acaaaaatca aaatgagcaa        60
aatcgttgct gtcgtcgtcc tagctgcctt ctgcgtagcc atgttggtca gcgatgtgtc       120
cgccaaaaca tcaatcagtg tcaaaggcga atcgaacgtg gatgtcgttt cccaaatcaa       180
cagtttggtt tcatctatcg tgtctggtgc caacgtgtca gcagtactcc tagctcaaac       240
tttagttaat atcctgcaaa ttcttatcga cgctaatgtt ttcgcttaat ttatatattc       300
tttagctttg tattgcgcgc atacaacgca ttcgaataaa gtaattaata aaattcaaaa       360
aaaaaaaaaa aaaaaaaaaa aa                                                382
```

IMMUNOSTIMULATORY COMPOSITIONS AND METHODS OF MANUFACTURE

RELATED APPLICATIONS

This application claims priority from NZ 599435 dated 17 Apr. 2012, the contents of which are incorporated herein by reference.

CROSS-REFERENCE TO RELATED APPLICATIONS

This application is the national phase of PCT application PCT/NZ2013/000070 having an international filing date of 17 Apr. 2013, which claims benefit of New Zealand patent application No. 599435 filed 17 Apr. 2012. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 730232000200SeqList.txt, date recorded: Nov. 30, 2015, size: 979 bytes).

TECHNICAL FIELD

Described herein are immunostimulatory compositions and methods of manufacture. More specifically, the compositions includes a combination of arabinogalactan protein (AGP) compounds, particularly those derived from honey or with similar activity to honey derived AGP's along with apisimin proteins, peptides or functional fragments thereof, particularly those isolated from royal jelly or apisimin produced via recombinant methods.

BACKGROUND ART

Immunostimulatory compounds are compounds that can encourage cytokine production and hence macrophage production, all being part of a normal immune system reaction observed in organisms. The main effects of immunostimulatory compounds result in the migration of macrophages to an inflamed area and an increase in (already existing) macrophage activity.

Inflammation relating to immune stimulation is often considered a negative reaction or a reaction to be avoided, particularly in the context of wound healing—i.e. why would you further inflame an already inflamed wound? The inventors have found that inflammation at least in the wound healing context is in fact beneficial for most wound applications contrary to that expected. As well as and distinct to anti-microbial effects, certain types of so-called 'active' honey appear to prime or kick start the immune system into action, a characteristic not uncommon in some contexts with positive outcomes e.g. to address chronic or recalcitrant infections where the natural wound healing process has stalled or alternatively, to prompt a reaction such as that observed when probiotic bacteria are introduced to the gut.

Many studies have also been produced showing how humans and animals react when their immune system is primed or kick started into action. For example, mice primed via an immune stimulatory challenge often survive another microbial challenge better than mice not primed. Many products utilising this priming function are administered orally, for example as lozenges, elixirs, sprays, tablets and capsules.

Arabinogalactan (AG) is a biopolymer consisting of arabinose and galactose monosaccharides. Two classes exist in nature being plant arabinogalactans and microbial arabinogalactans. In plants, AG is a major constituent of many gums including gum arabic, gum gutti and so on. AG is also found in Echinacea and other plant matter, typically in the amount of 0.1% weight or 100 µg/ml-200 µg/ml.

AG may be attached to proteins and the resulting arabinogalactan protein (AGP) functions as a signalling molecule between cells.

Honey derived AGP compounds appear to have immunostimulatory effects not seen in other types of AGP compounds. The activity of honey derived AGPs are described for example in WO2011/139168 (incorporated herein by reference), and the use of such compounds in a purified or concentrated form is also described illustrating the importance and commercial advantages of the activity of AGPs.

By contrast to the above, gum arabic-AGP and coffee-AGP have insignificant immunostimulatory effects, a finding somewhat surprising but which however illustrates how the specific proteins present in honey clearly have a very different effect on AGP activity.

Apisimin is one of three key functional proteins naturally found in royal jelly.

Royal jelly is a principal food of the honeybee queen and young female larvae. It is secreted from the hypopharyngeal and mandibular glands of honeybees. Royal jelly is often taken as a supplement for various nutritional benefits. Chemical analysis of royal jelly has shown that royal jelly from honey bees (*Apis* species) consists mainly of proteins (12-15%) which constitute about 50% of its dry mass. Royal jelly also includes carbohydrates (10-16%), lipids (3-6%), vitamins and free amino acids, together with several bioactive substances. Besides apisimin, the other two key functional peptides are apalbumin and royalisin.

A number of papers exist in regard to apalbumin and royalisin, which teach about the activity of these peptides and their make-up as well as processes of extraction and recombinant manufacture.

Apisimin by contrast is relatively poorly researched although one paper, Bilikova et al FEBS Letters 528 (2002) 125-129 describes apisimin as being a new serine-valine rich peptide and also describes purification and molecular characterisation methods. Apisimin is described as being a 5.5 kDa sized molecule having 54 amino acids. The paper gives nucleotide and encoded amino acid sequences for apisimin.

It should be appreciated from the above that it would be useful to have improved immunostimulatory compositions and methods of manufacture and/or at least provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art, in New Zealand or in any other country.

For the purpose of this specification the term 'comprise' and grammatical variations thereof shall have an inclusive meaning—i.e. that it will be taken to mean an inclusion of not only the listed components it directly references, but also other non-specified components or elements.

Further aspects and advantages of the process and product will become apparent from the ensuing description that is given by way of example only.

SUMMARY

Described herein are immunostimulatory compositions including a combination of honey-derived or honey-like AGP along with isolated and/or purified apisimin proteins, peptides or functional fragments thereof.

The inventors have unexpectedly found that the combination of honey derived AGP compounds and apisimin peptides act to stimulate the immune system of a subject. This stimulation effect is far greater than the individual components themselves. This synergism is not predictable from the art and appears to relate to the binding characteristics of honey derived AGP compounds and apisimin. The stimulation effect appears to be highly synergistic. For example, only a lower amount of product may be required in order to achieve the desired stimulatory effects and the stimulation effect goes beyond what either of the components achieve alone.

In a first aspect there is provided an immunostimulatory composition including a therapeutically effective amount of:
  a) honey derived AGP; and
  b) isolated and/or purified apisimin proteins, peptides or functional fragments thereof.

In a second aspect there is provided a method of stimulating the immune system of a subject by administration of a composition including a therapeutically effective amount of:
  a) honey derived AGP; and
  b) isolated and/or purified apisimin proteins, peptides or functional fragments thereof.

In a third aspect there is provided the use of an immunostimulatory composition including a therapeutically effective amount of:
  a) honey derived AGP; and
  b) isolated and/or purified apisimin proteins, peptides or functional fragments thereof in the manufacture of a medicament that, on administration, stimulates the immune system of a subject.

In a fourth aspect there is provided a method of manufacturing an immunostimulatory composition substantially as described above by the steps of:
  a) testing the concentration of AGP in a selection of honeys, honey fractions, or honey isolates batch samples;
  b) testing the concentration of apisimin proteins, peptides or functional fragments thereof in the selection of honeys, honey fractions or honey isolates batch samples; and
  c) selecting and blending the batches in order to maximise the AGP and apisimin concentrations in a final composition.

The method substantially as described above wherein the AGP and apisimin concentrations are measured via Enzyme Linked Immuno Sorbent Assay (ELISA) analysis.

The inventors have determined that the combination of honey derived AGP compounds and apisimin peptides act to stimulate the immune system of a subject. The AGP may be in honey or isolated/concentrated. The apisimin may be isolated from royal jelly and/or isolated/concentrated or via recombinant methods. The inventors have discovered that the combination royal jelly itself (containing apisimin) and honey derived AGP compounds surprisingly do not act to stimulate the immune system of a subject. By contrast, in an isolated form or at least absent of apalbumin and royalisin has useful immune stimulation effects.

Also, the inventors have identified that this stimulatory effect is far more than just an additive effect and there appears to be a considerable synergy resulting from the combination of honey derived AGP compounds and apisimin peptides. This synergy is at least twice that expected from either component alone as defined by the cytokine tumour necrosis factor (TNF)-α production.

The same synergy is not observed for all AGP's—by way of example, gum based AGP compounds do not have any inherent immunostimulatory effects. When apisimin is added, the only observed immunostimulatory effects are from apisimin alone and no synergy or higher level is observed.

Advantages of the above compositions, methods and uses include the ability to achieve synergistic immunostimulatory effects. The synergism means that a lower amount of product may be required in order to achieve the desired stimulatory effects. The synergy also means that a lower amount of raw materials may be required to achieve the same effect as with one or the other compound alone.

BRIEF DESCRIPTION OF THE DRAWINGS

Further aspects of the compositions, methods and uses will become apparent from the following description that is given by way of example only and with reference to the accompanying drawings in which.

DETAILED DESCRIPTION

As noted above, immunostimulatory compositions are described herein including a combination of honey-derived or honey-like AGP along with apisimin proteins, peptides or functional fragments thereof.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' refers to at least about 50%, for example 75%, 85%, 95% or 98%.

For the purposes of this specification, the term 'arabinogalactan' or 'AG' or grammatical variations thereof refers to biopolymers containing arabinose and galactose monosaccharides.

The term 'type II' when used in reference to AG compounds refers to a family of highly branched polysaccharide compounds rich in galactose and arabinose. They consist of a (1-3)-β-D-galactan backbone having (1-6)-β-D-galactan side chains, which in turn are modified by arabinose. Short arabinose oligosaccharide chains may additionally decorate the galactan backbone.

The term 'arabinogalactan protein' or 'AGP' or grammatical variations thereof refers to arabinogalactan compounds where the polysaccharide units are attached to multiple sites on a core protein, rich in hydroxyproline.

For the purposes of this specification, the terms 'honey' and 'honey with naturally derived AGP' refers to naturally produced honey (i.e. produced by bees) containing at least a mix of glucose, fructose, water, glucose oxidase enzyme and AGP.

The term 'honey analogue' refers to a mixture of 30-50% glucose, 30-50% fructose, 1-18% water and either or both of glucose oxidase enzyme and/or hydrogen peroxide. Where the analogue is used shortly after production, hydrogen peroxide itself may be used. Where the analogue may be stored for a period of time, the analogue by preference contains glucose oxidase enzyme. As may be appreciated, glucose oxidase enzyme converts sugars into hydrogen peroxide that also results in a lower pH. If hydrogen peroxide alone is used and then the analogue stored, it is possible that the peroxide level will decrease by a normal reduction equilibrium and the pH level then increase. Using glucose oxidase enzyme ensures a steady level of hydrogen peroxide and hence steady pH. The quantities used are intended to approximate the composition of naturally produced honey.

The term 'honey fraction' refers to a naturally produced honey where substantially all of the monosaccharide portion of the honey has been removed to produce a honey fraction. The monosaccharide portion may include fructose and glucose. Honey fractions referred to in this specification include a UMF or non-peroxide activity containing portion of the honey as well as other non-saccharide components including compounds selected from: phenolics, bee defensins, and catalase enzyme.

The term 'gelling agent' or grammatical variations thereof refers to an agent that, in the absence of liquid is not a gel, but the agent is able to form a gel in the presence of liquid.

The term 'dressing' refers to any covering that may be applied to a lesion where lesions encompass infected and non-infected abrasions, cuts, bits, burns, wounds, ulcers, abscesses, surgical wounds, fungating tumours and pressure sores.

The term 'therapeutically effective' with reference to an amount or dosage of a composition or medicament noted refers to an amount of a composition that is sufficient to effectively stimulate the immune system of a subject. However, this term should not be seen as limiting as 'therapeutically effective' may refer to an amount or dosage of a composition or medicament that optimises the immunostimulatory effects on a subject depending on desired application. For example, an amount or dosage of a composition or medicament where minimal or no inflammation is desired.

The term 'isolate' or grammatical variations thereof refers to a composition containing an active concentration of AGP compounds separated or isolated from a honey and/or an active concentration of apisimin proteins, peptides or functional fragments thereof separated or isolated from an apisimin source.

The term 'immunostimulatory', 'stimulate' 'pro-inflammatory' or grammatical variations thereof refer to the subject's immune system being activated to the extent that macrophage cells are present at a wound site or equivalent and produce cytokines consistent with an inflammatory response including but not limited to TNF-α, IL-6 and IL-10.

The term 'topical' refers to placement on a body area of a subject such as skin as well as mucosal areas such as the oral cavity e.g. gums, the nasal cavity and the vaginal cavity. The term may also encompass the intestine wall owing to the fact that type II AG compounds are comparatively stable and on oral delivery would reach the intestines chemically intact.

The terms 'chronic' or 'recalcitrant' are used interchangeably to refer to a skin area or broken skin area such as a burn or wound that is either not healing or is only healing slowly despite treatment. This style of healing may be characterised by little macrophage activity at or around the skin area.

The term 'sensitive' or grammatical variations thereof refers to a skin area that the subject finds particularly painful.

The terms 'prime the immune system' and/or 'stimulate the immune system' refer to the presence of macrophage cells producing or capable of producing inflammatory related cytokines.

In a first aspect there is provided an immunostimulatory composition including a therapeutically effective amount of:
  a) honey derived AGP; and
  b) isolated and/or purified apisimin proteins, peptides or functional fragments thereof.

The inventors have unexpectedly found that the combination of honey derived AGP compounds and apisimin peptides act to stimulate the immune system of a subject. This stimulation effect is far greater than the individual components themselves. This synergism is not predictable from the art and appears to relate to the binding characteristics of honey derived AGP compounds and apisimin. The stimulation effect appears to be highly synergistic. For example, only a lower amount of product may be required in order to achieve the desired stimulatory effects and the stimulation effect goes beyond what either of the components achieve alone.

The honey derived AGP may be in a form selected from: honey with naturally derived AGP; AGP isolated and/or purified from honey; an AGP containing honey fraction; an AGP containing honey isolate; an AGP containing honey analogue; and combinations thereof.

The honey analogue may include a honey fraction containing AGP.

The honey analogue may include a honey isolate containing AGP.

In preferred embodiments, the apisimin excludes substantially all other proteins or peptides found in royal jelly. This appears to be counterintuitive and the experimental results demonstrate royal jelly itself (containing apisimin) to have a quenching effect on the immunostimulatory system. Unexpectedly, the inventors have found that the combination of royal jelly itself (containing apisimin) and honey derived AGP compounds do not act to stimulate the immune system of a subject. By contrast, in an isolated form or at least absent of apalbumin and royalisin has useful stimulation effects.

The purified apisimin proteins, peptides or functional fragments thereof may be isolated from royal jelly. The royal jelly used may be a royal jelly with greater natural concentrations of apisimin. Like for the case of honey, royal jelly varies in peptide concentration between hives and other factors may be at play also not yet fully exemplified. Maximising the apisimin concentration for use in the above compositions, methods or uses may be of benefit to increase medical (stimulatory) activity and/or to minimise the amount of raw material required.

The apisimin may be produced via recombinant methods using microbes such as *E. coli* or may be produced by chemical synthesis. Recombinant methods to produce apisimin are described in the art and may be commercially useful methods of production in order to increase product volumes and minimise natural variation.

Royal jelly production (and hence apisimin production) may be increased naturally by removal of a queen bee from a hive or threatening the survival of the queen in the hive thereby stimulating royal jelly production.

The apisimin sequence may be found in Bilikova et al FEBS Letters 528 (2002) 125-129 and is set forth in SEQ ID NO. 1. The sequence may have at least 70%, or 75%, or 80%, or 85%, or 90%, or 95% homology with the apisimin sequence may be that found in Bilikova et al FEBS Letters 528 (2002) 125-129.

The concentration of AGP in the honey derived AGP in the compositions described above may be 1, or 2, or 3, or 4, or 5, or 6, or 7, or 8, or 9, or 10, or 11, or 12, or 13, or 14, or 15, or 16, or 17, or 18, or 19, or 20 µg/ml. The concentration may be at least 1 µg/ml.

The composition may contain type II arabinogalactan (AG) protein.

The concentration of apisimin proteins, peptides or fragments thereof isolated in the compositions described above may be 5, or 10, or 15, or 20, or 25, or 30, or 35, or 40, or 45, or 50 µg/ml. The concentration may be at least 5 µg/ml.

The extent of stimulation appears to be dose dependent. By way of illustration, a combination of 5 µg/ml of honey derived AGP and 25 µg/ml apisimin gives a TNF-α response after 4 hours of approximately 1600 µg/ml. In comparison a 100 ng/ml dose of lipopolysaccharide (LPS) produces a TNF-α response after 4 hours of approximately 1700 µg/ml, a response, being remarkably close to that generated from the synergistic combination of AGP and apisimin. Apisimin alone only produces a TNF-α response in the order of 700 pg/ml after 4 hours and AGP alone only produces a TNF-α response in the order of 200 pg/ml after 4 hours, both individual components falling well short of the combination activity. Even an additive response still does not reach the stimulatory levels observed for the combination.

The above compositions may be formulated for oral or topical delivery to a subject. Oral formulations may include lozenges, elixirs, liquids, sprays, gels, ointments, tablets, and capsules. Topical formulations may be formulated as liquids, gels, ointments or semi-solid or solid putties or sheets.

The subject may be human. Alternatively, the subject may be a non-human animal. As should be appreciated, humans and animals can equally be treated using the immunostimulatory composition as the physiology of an immune response may be similar between humans and at least mammals. Non-limiting examples of animals to which the composition may be administered includes horses, livestock including cattle, sheep and deer and companion animals such as cats and dogs.

The compositions may be used for a wide variety of applications. Some illustrative examples may include: to prime the immune system on an on-going basis to prevent infection; as a cosmetic facial preparation to tighten or plump the skin and minimise wrinkles; as a travel remedy to help with jet lag and address unknown microbial challenges; as a wound dressing either externally or internally to assist healing. The composition appears to prime or kick start the immune system into action via a second phase of healing, a characteristic not uncommon in some contexts with positive outcomes e.g. to address chronic or recalcitrant infections where the natural wound healing process has stalled for some reason or alternatively to prompt a positive reaction such as that observed when probiotic bacteria are introduced to the gut.

The composition substantially as described above may be incorporated into a wound dressing.

As should be appreciated, wound dressings and aqueous based medicaments incorporating honey are well known and researched. Examples include those described in at least U.S. Pat. No. 7,714,183, U.S. Pat. No. 6,956,144, U.S. Ser. No. 11/106,473, U.S. Ser. No. 12/091,897 and U.S. Ser. No. 12/301,931. The immunostimulatory combination described herein and the synergies that the combination provides in stimulating the immune system have considerable power to improve current wound dressings and medicaments.

The dressing or aqueous based medicament may include at least one gelling agent. As noted above and in the art, gelling agents are advantageous for use with honey for wound applications. In particular, the gelling agents reduce the tackiness of the honey, yet provide a more cohesive structure such as a sheet structure or viscous gel that is easier to apply to a wound, skin region or mucosal lining. Gelling agents also have the advantage that they may be absorbent and work to move exudate away from a wound environment. This consequently avoids dilution of the honey and apisimin at the site.

The gelling agent may be selected from: an absorbent synthetic polymer, an absorbent natural based polymer, and combinations thereof.

The absorbent synthetic polymer may be selected from: any cross-linked sodium polyacrylate, polyacrylamide copolymer, ethylene maleic anhydride copolymer, carboxymethyl cellulose, polyvinyl alcohol copolymer, isobutylene-maleic anhydride copolymer, cross-linked polyethylene oxide, starch grafted copolymer or polyacrylonitrile, gauze, and combinations thereof.

The absorbent natural based polymer may be selected from: alginate, agar, natural based gums, and combinations thereof.

In the above embodiment where alginate is used, the alginate may be selected from: calcium alginate, sodium alginate, and combinations thereof.

In a second aspect there is provided a method of stimulating the immune system of a subject by administration of a composition including a therapeutically effective amount of:
 a) honey derived AGP; and
 b) isolated and/or purified apisimin proteins, peptides or functional fragments thereof.

In the above method, the honey derived AGP may be in a form selected from: honey with naturally derived AGP; AGP isolated and/or purified from honey; an AGP containing honey fraction; an AGP containing honey isolate; an AGP containing honey analogue; and combinations thereof.

The apisimin in the above method may include isolated and/or purified apisimin proteins, peptides or functional fragments thereof isolated from royal jelly.

The apisimin in the above method may include isolated and/or purified apisimin proteins, peptides or functional fragments thereof produced synthetically via recombinant methods using microbes such as *E. coli* or may be produced by chemical synthesis.

In a third aspect there is provided the use of an immunostimulatory composition including a therapeutically effective amount of:
a) honey derived AGP; and
b) isolated and/or purified apisimin proteins, peptides or functional fragments thereof in the manufacture of a medicament that, on administration, stimulates the immune system of a subject.

In the above use, the honey derived AGP may be in a form selected from: honey with naturally derived AGP; AGP isolated and/or purified from honey; an AGP containing honey fraction; an AGP containing honey isolate; an AGP containing honey analogue; and combinations thereof.

The use may include isolated and/or purified apisimin proteins, peptides or functional fragments thereof isolated from royal jelly.

The apisimin in the above use may include isolated and/or purified apisimin proteins, peptides or functional fragments thereof produced synthetically via recombinant methods using microbes such as *E. coli* or may be produced by chemical synthesis.

As noted above, the combination of honey derived AGP compounds and apisimin act to stimulate the immune system of a subject. The inventors have identified that this effect is far more than just a cumulative effect and there appears to be a considerable synergy resulting from the combination. This synergy may be at least 1.5, for example, at least 1.75, or 2.0, or 2.25, or 2.5 times that expected from either component alone as defined by the cytokine TNF-α production.

The same synergy may not be observed for all derivations of AGP. By way of example, gum based AGP compounds do not have any inherent immunostimulatory effects. When apisimin is added, the only observed immunostimulatory effects are from apisimin alone and no synergy or higher level is observed.

The reason for the synergy is not fully established, however without being bound by theory the inventors consider that apisimin self-binding may be important in providing multi-valency for interaction with a receptor on the surface of monocytes. Apisimin is understood to bind to a cell-surface receptor whereas AGP is thought to bind to a toll-like receptor. The synergy observed is envisaged as being due to the combination of pathways activated. Whatever the mechanism, the inventors have observed that when two binding molecules act simultaneously as in the above compositions challenge immune cells, the cells respond disproportionately high when compared with a single challenge.

In a fourth aspect there is provided a method of manufacturing an immunostimulatory composition substantially as described above by the steps of:

a) testing the concentration of AGP in a selection of honeys, honey fractions, or honey isolates batch samples;
b) testing the concentration of apisimin proteins, peptides or functional fragments thereof in the selection of honeys, honey fractions or honey isolates batch samples; and
c) selecting and blending the batches in order to maximise the AGP and apisimin concentrations in a final composition.

The AGP and apisimin concentrations may be measured via Enzyme Linked Immuno Sorbent Assay (ELISA) analysis.

Selection and blending may be completed so that:
a) the concentration of AGP in the composition is greater than approximately 1 µg/ml; and
b) the concentration of apisimin proteins, peptides or functional fragments thereof in the composition is greater than approximately 5 µg/ml.

The concentration of AGP in the honey or isolated may be 0.5, or 0.6, or 0.7, or 0.8, or 0.9, or 1, or 2, or 3, or 4, or 5, or 6, or 7, or 8, or 9, or 10, or 11, or 12, or 13, or 14, or 15, or 16, or 17, or 18, or 19, or 20 µg/ml. The concentration may be at least 1 µg/ml.

The concentration of apisimin proteins, peptides or fragments thereof may be 5, or 10, or 15, or 20, or 25, or 30, or 35, or 40, or 45, or 50 µg/ml. The concentration may be at least 5 µg/ml.

ELISA may be a useful detection protocol to select and blend a honey composition with increased apisimin for use as an immune stimulatory composition as it is easily implemented in a QA laboratory, can be used to process many samples at once (40-80), provides accurate results and gives a useful degree of detection limit. The use of ELISA is known for the detection of AGPs. However, these established protocols are designed to test AGPs in plant extracts or bodily fluids.

The inventors found that honey with its high sugar concentration and complex composition gave unique characteristics, very distinct from the above plant extracts or bodily fluids. The mere replication of known ELISA protocols did not provide accurate results and it was found necessary to test and optimise each step of the ELISA protocol for the use with honey.

The establishment of a suitable honey AGP-ELISA method or protocol involved complex and non-obvious experimentation where ingenuity was required to overcome and provide solutions to some of the following problems and/or unknown factors: the ability of honey to bind to the material of a microtitetplate (e.g. polystyrene), honey components not present in plant derived samples interfering with the binding process, honey components interfering with Bovine Serum Albumin (used as a blocking agent), the cross reactivity of honey components with the tested Anti-AGP antibodies raised against common plants (e.g. carrots), the viability of honey AGPs to have epitope regions to allow the binding of common Anti-AGP antibodies, and honey components interfering with the alkaline phosphatase detection method.

For the honey AGP-ELISA method developed, the inventors discovered that although diluted complete honeys may be tested, the results appear to have low accuracy.

In preferred embodiments, the honey AGP-ELISA method may include ultrafiltration of the honeys, honey fractions, or honey isolates to obtain a high molecular weight fraction wherein components approximately less than or equal to 5 kDa are removed. The removal of components less than 5 kDa such as glucose, fructose and other smaller sugars results in an accurate measurement of AGP concentration during analysis.

In the case of the apisimin-ELISA method or protocol it is known for the detection of protein concentration. However, the apisimin-ELISA method developed by the inventors has allowed for specific monoclonal anti-apisimin antibodies to be developed to successfully test in an ELISA protocol against apisimin.

The honey or honey isolate and/or apisimin proteins, peptides or functional fragments thereof may be further processed by steps selected from: filtration, ultrafiltration, reverse osmosis, solvent extraction, precipitation, or combinations thereof and collecting a high molecular weight isolate from the processing step.

In the above embodiment, the honey or honey isolate and/or apisimin proteins, peptides or functional fragments thereof may be filtered and the high molecular weight fraction collected so as to increase the concentration of AG and/or apisimin in the high molecular weight isolate. In one embodiment, honey and/or apisimin may be filtered to obtain a high molecular weight fraction via a 5 kDa filter. In an alternative embodiment, the filter size may be via a 10 kDa filter. In an alternative embodiment, the filter size may be a 20-30 kDa filter.

The honey used in the composition or the honey from which the AGP is derived may be selected from honeys with greater natural concentrations of AGP. The honey may be selected from substantially kanuka and/or manuka floral origin honeys and/or nectars. As noted in WO2011/139168, not all honeys produce the same amount of AGP. Selecting honeys with a floral origin of greater concentration AGP can therefore increase the immunostimulatory response. Kanuka honey is a honey known to contain more AGP compounds than others. Manuka honey is also a useful source although less so than kanuka.

The honey from which the AGP is derived may be selected from honeys derived from the plant genus *Leptospermum, Kunzea, Weinmannia, Knightia, Metrosideros, Fagus, Trifolium, Myrtaceae*, and combinations thereof. In selected embodiments as above, the honey may be of manuka origin. The honey may be of kanuka origin. The honey may be of clover origin. The honey may instead be a multifloral honey.

The AGP's may be produced via recombinant plant tissue culturing with or without post translational modification. As should be appreciated, production of AGP solely from honey is not essential to the invention. Instead, AGP compounds may be produced artificially via recombinant technologies. As the honey based AGP is largely plant derived, it is envisaged that recombinant technologies would utilise plant tissue cultures or plants selected for and bred for AGP content in order to manufacture the AGP artificially.

The AGP concentration in honey may be increased by filtration and/or centrifuge separation. A variety of techniques are already known for isolating AGP from honey and these methods are envisaged to be equally applicable to the present invention.

Advantages of the above compositions, methods and uses include the ability to achieve synergistic immunostimulatory effects. The synergism means that a lower amount of product may be required in order to achieve the desired stimulatory effects. The synergy also means that a lower amount of raw materials may be required to achieve the same effect as with one or the other compound alone. Also, it has been found that the use of royal jelly itself (containing apisimin) in combination with honey derived AGP is counterintuitive as royal jelly does not simulate the immune system, yet isolated apismin from the royal jelly in combination results in synergistic immunostimulatory effects.

As should be appreciated, the above embodiments approach the understanding of optimising the immunostimulatory potential of the above compositions, methods and uses. However, this should not be seen as limiting as the converse may be true where an inflammatory or an elevated immunostimulatory response may cause considerable pain and discomfort to the subject.

In alternative embodiments, an object of the invention may be to provide compositions as substantially described above by methods as substantially described above, but where the compositions are selected to include a low concentration of honey derived AGP and apisimin. For example, the composition may be formulated for application to a sensitive topical body area on a patient where minimal or no inflammation is desired. A specific non-limiting example may be a combination honey and royal jelly skin care product for sensitive skin or if used in an already healing wound in which increased inflammation is not desirable.

In one embodiment of the above, the concentration of honey derived AGP may be less than 1 µg/ml and concentration of apisimin proteins, peptides or fragments thereof may be less than 5 µg/ml respectively.

The embodiments described above may also be said broadly to consist in the parts, elements and features referred to or indicated in the specification of the application, individually or collectively, and any or all combinations of any two or more said parts, elements or features, and where specific integers are mentioned herein which have known equivalents in the art to which the embodiments relates, such known equivalents are deemed to be incorporated herein as of individually set forth, Where specific integers are mentioned herein which have known equivalents in the art to which this invention relates, such known equivalents are deemed to be incorporated herein as if individually set forth.

WORKING EXAMPLES

The above described compositions, methods and use are now described by reference to specific examples.

Example 1

As noted above, the inventors consider that apisimin may work synergistically on the basis that apisimin self binds to more complex molecules. Apisimin self-binding may be important in providing multi-valency for interaction with a receptor on the surface of monocytes. Apisimin is understood to bind to a cell-surface receptor whereas AGP is thought to bind to a toll-like receptor. The synergy observed is envisaged as being due to the combination of pathways activated.

Figure 1:
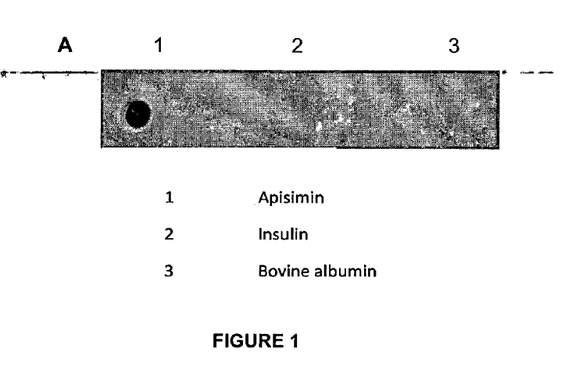
FIG. 1 illustrates the results of a dot blot assay to test the self binding properties of apisimin against two other proteins not know to be self binding being insulin and bovine albumin. 1=apisimin, 2=insulin, 3=bovine albumin. The darker the colour the greater the degree of binding.

An experiment was conducted to confirm the self-binding nature of apisimin versus other peptides being insulin and bovine albumin. As can be seen in FIG. 1, the apisimin is clearly strongly self binding as evidenced by the dark blot versus insulin and albumin that are weak or not self binding where the blot is light coloured.

Example 2

The self binding nature of apisimin was further investigated. AGP is known to be present in honey but at varying concentrations depending on the floral origin of the honey.

Kanuka has greater concentrations of AGP, manuka honey less so while clover honey has minimal if any AGP present, the AGP typically being donated from the plant nectar.

Figure 2:
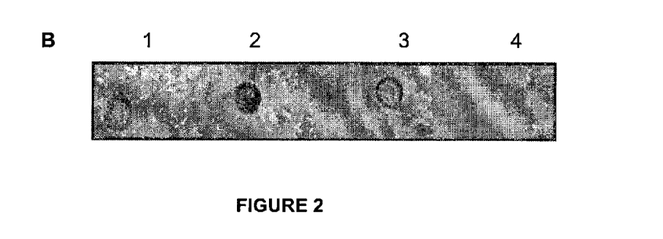
FIG. 2 illustrates a further dot blot assay comparing the degree of self binding occurring when apisimin at the same concentration is combined with four different floral origin honeys, 1=kanuka, 2=manuka, 3=clover, 4=blank (control). Darker colours represent greater levels of binding.

As shown in FIG. 2, the degree of self binding by apisimin within the honey samples varied according to the concentration of AGP in the honey. Kanuka honey showed the darkest blot corresponding with the highest concentration of AGP, manuka less so although still a significant blot while clover honey showed little blotting corresponding to the low concentration of AGP present in clover honey.

Example 3

The immunostimulatory effect was then tested using a variety of samples. Prior to the trial a monocyte cell culture was produced in order to eliminate any natural variation errors. The monocyte culture was then stimulated using a variety of agents and TNF-$\alpha$ concentration measured after 4 hours of treatment with the various reagents.

LPS was used as a positive control being a known and strongly significant stimulant. Cells alone were used as a negative control.

Figure 3:
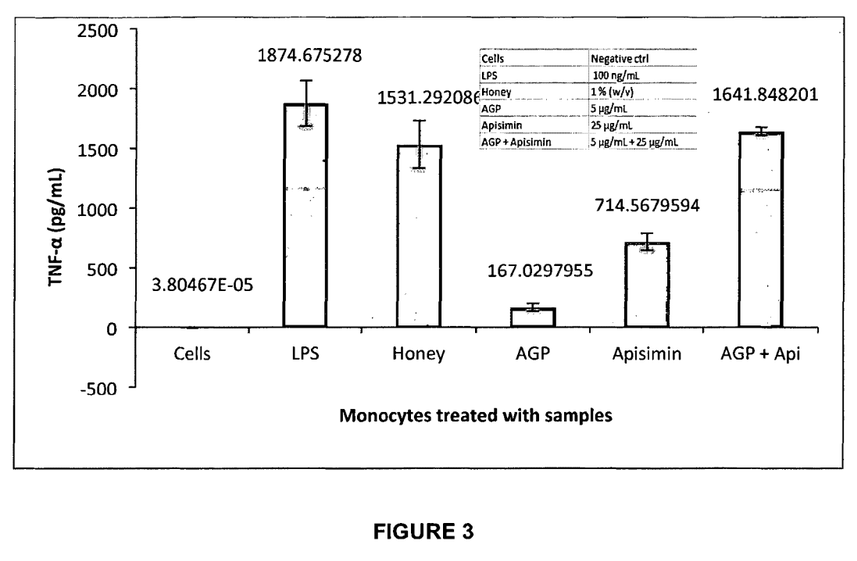
FIG. 3 illustrates the TNF-α response from a monocyte cell line due to various agents, LPS being a positive control, cells alone being a negative control.

As shown in FIG. 3, AGP and apisimin alone have stimulatory effects of 167.0297955 and 714.5679594 pg/mL of TNF-$\alpha$ respectively. The combination effect though of 1641.848201 pg/mL of TNF-$\alpha$ was observed to be significantly higher than each individual compound and well higher than even an additive effect therefore illustrating a considerable synergy.

The self binding nature of apisimin is thought to be important as this function in tandem with that from AGP gives a far greater effect than would otherwise be the case.

Example 4

Figure 4:
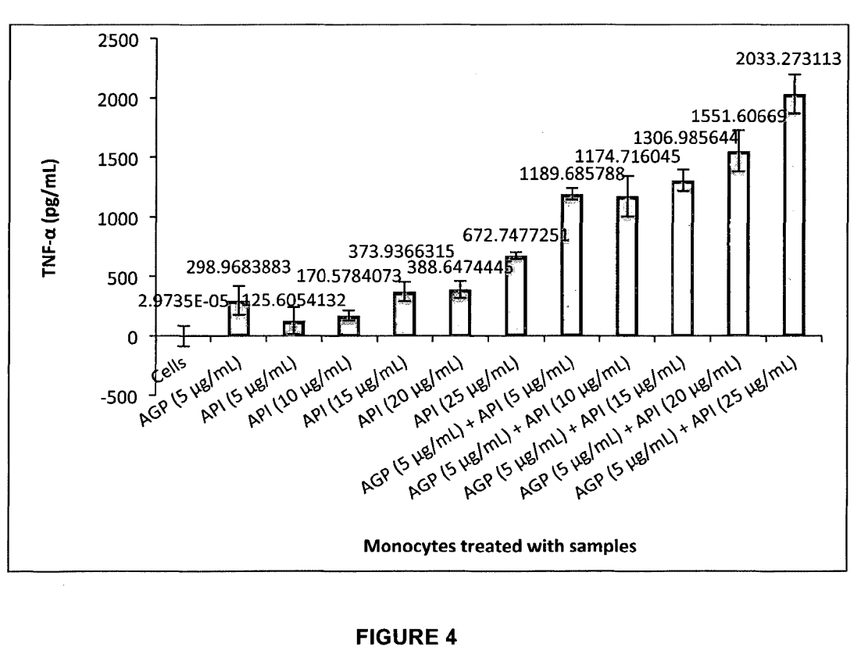
FIG. 4 illustrates a dose response trial using varying amounts of AGP and apisimin.

The effects of apisimin on TNF-$\alpha$ release were concentration-dependent. To explore the relationship between apisimin and AGP further, increasing concentrations of apisimin were used to stimulate blood monocytes in the presence of a constant concentration of kanuka honey AGP (5 µg/mL) (FIG. 4). The synergistic effects of apismin with AGP were also concentration-dependent. For example, stimulation with 5 µg/mL AGP and 25 µg/mL of apisimin caused the release of 2033.27311 pg/mL of TNF-$\alpha$, whereas together the stimulants alone caused the release of only 298.968 pg/mL and 672.7477 pg/mL of TNF-$\alpha$ respectively i.e. effectively a doubling of TNF-$\alpha$ release.

Example 5

The immunostimulatory effect was tested further using a variety of samples including royal jelly. Prior to the trial a monocyte cell culture was produced in order to eliminate any natural variation errors. The monocyte culture was then stimulated using a variety of agents and TNF-$\alpha$ concentration measured after 4 hours of treatment with the various reagents.

LPS was used as a positive control being a known and strongly significant stimulant. Cells alone were used as a negative control.

Figure 5:
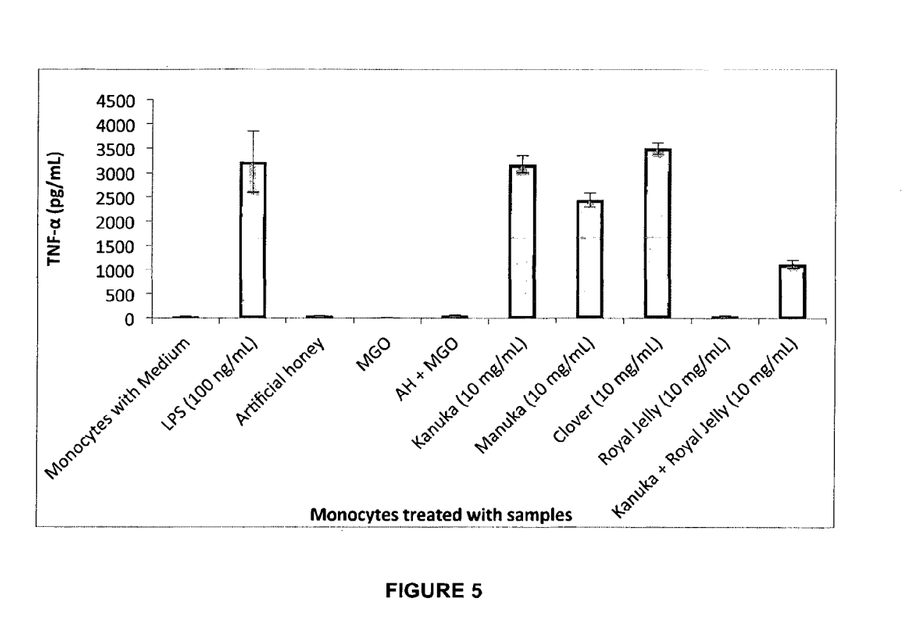
FIG. 5 illustrates the TNF-α response from a monocyte cell line due to various agents, such as honeys, royal jelly, combinations thereof, and LPS being a positive control, cells alone being a negative control.

As shown in FIG. 5, not all honeys produce the same amount of AGP. Selecting honeys with a floral origin of greater concentration AGP can therefore increase the immunostimulatory response. From the results, Kanuka honey contains more AGP compounds than Manuka honey although it is still a useful source.

It is known that royal jelly contains apisimin. However, the inventors have discovered that royal jelly alone and the combination royal jelly itself along with a honey derived AGP compound surprisingly do not act to stimulate the immune system of a subject. The apisimin is first required to be isolated from the royal jelly. For example, stimulation with royal jelly 10 mg/mL caused negligible release of 48.287 pg/mL of TNF-$\alpha$, whereas together the stimulants of Kanuka and royal jelly caused the release of only 1118.0031 pg/mL compared to Kanuka alone with a release of 3177.1245 pg/mL of TNF-$\alpha$.

Example 6

The immunostimulatory effect was tested further using a variety of honey derived AGP compounds and apisimin. Prior to the trial a monocyte cell culture was produced in order to eliminate any natural variation errors. The monocyte culture was then stimulated using a variety of agents and TNF-$\alpha$ concentration measured after 4 hours of treatment with the various reagents.

Figure 6:
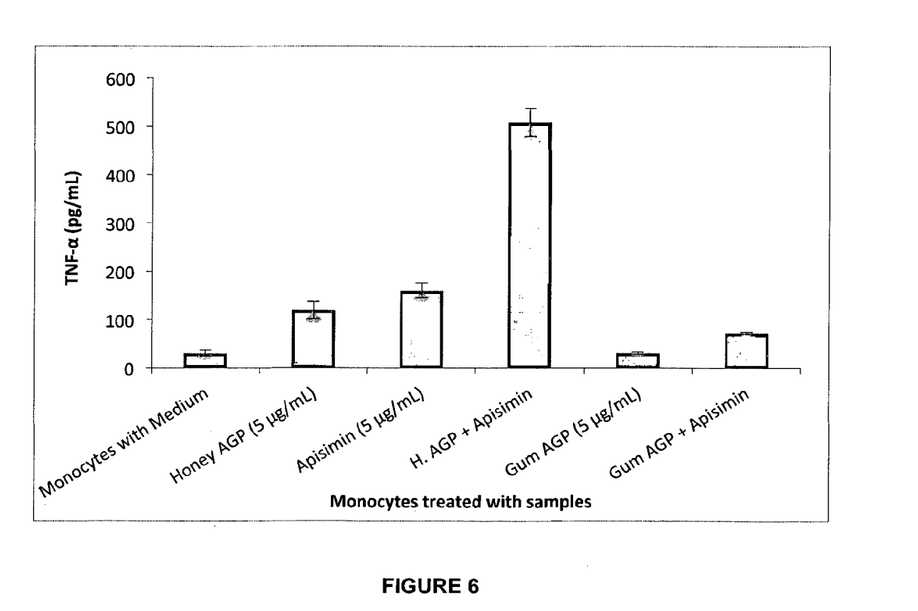
FIG. 6 illustrates the TNF-α response from a monocyte cell line due to derivatives of AGP, and cells alone being a negative control.

As shown in FIG. 6, Honey AGP (5 µg/mL) and apisimin (5 µg/mL) alone have stimulatory effects of 119.13625 and 160.463227 pg/mL of TNF-$\alpha$ respectively. The combination effect though of 507.84476 pg/mL of TNF-$\alpha$ was observed to be significantly higher than each individual compound and well higher than even an additive effect therefore illustrating a considerable synergy.

Again, the self-binding nature of apisimin is thought to be important as this function in tandem with that from AGP gives a far greater effect than would otherwise be the case.

The same synergy may not be observed for all derivations of AGP. By way of example gum based AGP compounds with a release of 31.02954 pg/mL of TNF-$\alpha$ do not have any inherent immunostimulatory effects. When apisimin is added, the only observed immunostimulatory effects are from apisimin alone and no synergy or higher level is observed. A finding somewhat surprising but which however illustrates how the specific proteins present in honey clearly have a very different effect on AGP activity.

Example 7

The immunostimulatory effect was tested further using a honey derived AGP compound, apisimin and Polymyxin B acting as an LPS inhibitor. Prior to the trial a monocyte cell culture was produced in order to eliminate any natural variation errors. The monocyte culture was then stimulated using a variety of agents and TNF-$\alpha$ concentration measured after 4 hours of treatment with the various reagents.

Figure 7:
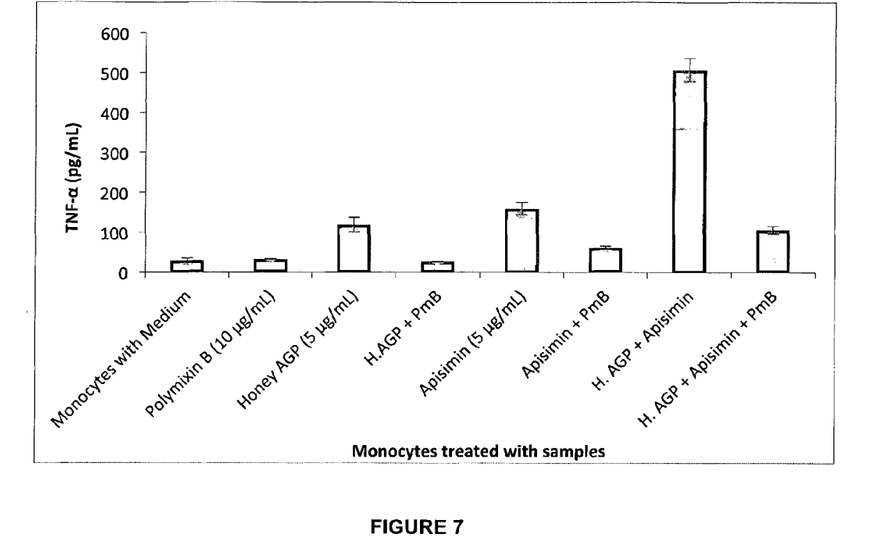
FIG. 7 illustrates the TNF-α response from a monocyte cell line due to various honey derivatives of AGP, abrogation by Polymyxin B, and cells alone being a negative control.
Figure 8:
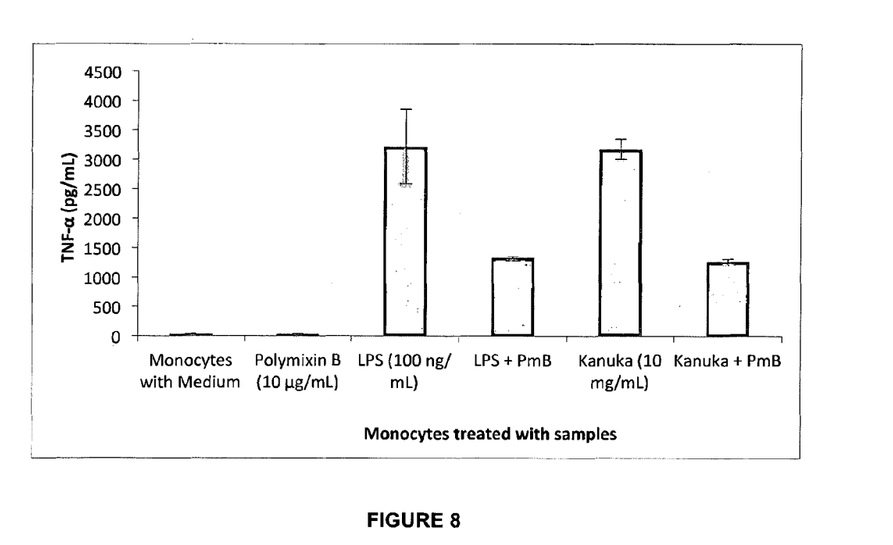
FIG. 8 illustrates the TNF-α response from a monocyte cell line due to kanuka honey, LPS being a positive control, abrogation by Polymyxin B, and cells alone being a negative control.

As above for Example 6 and shown in FIG. 7, Honey AGP (5 µg/mL) and apisimin (5 µg/mL) alone have stimulatory effects of 119.13625 and 160.463227 pg/mL of TNF-$\alpha$ respectively. The combination effect though of 507.84476 pg/mL of TNF-$\alpha$ was observed to be significantly higher than each individual compound and well higher than even an additive effect therefore illustrating a considerable synergy. However, the immunostimulatory effect is abrogated in each case with the addition of Polymyxin B acting as an LPS inhibitor.

Example 8

The immunostimulatory effect was tested further using Kanuka honey and Polymyxin B. Prior to the trial a monocyte cell culture was produced in order to eliminate any natural variation errors. The monocyte culture was then stimulated using a variety of agents and TNF-α concentration measured after 4 hours of treatment with the various reagents.

LPS was used as a positive control being a known and strongly significant stimulant. Cells alone were used as a negative control.

As per the results shown in Example 7 above, the immunostimulatory effect is abrogated in each case with the addition of antibiotic Polymyxin B.

Example 9

The AGP content in different honeys was tested utilising the honey AGP-ELISA protocol established for this invention as follows:

Honeys were diluted in Phosphoric Buffer Saline and pipetted into wells of a microtiterplate made of polystyrene. After incubation at room temperature for 2 hours, the plate was washed with washing buffer to remove unbound material. Afterwards, the plate was blocked with Bovine Serum Albumin to prevent unspecific binding of antibodies. The plate was incubated overnight with JIM 13 (an antibody against carrot AGPs) and washed the next morning. The amount of bound JIM 13 was detected with an alkaline phosphatase marked secondary antibody and after washing again the amount of bound secondary antibody was detected by conversion of Para-Nitrophenyl-phosphate and measurement of the resulting colour change.

Figure 9:
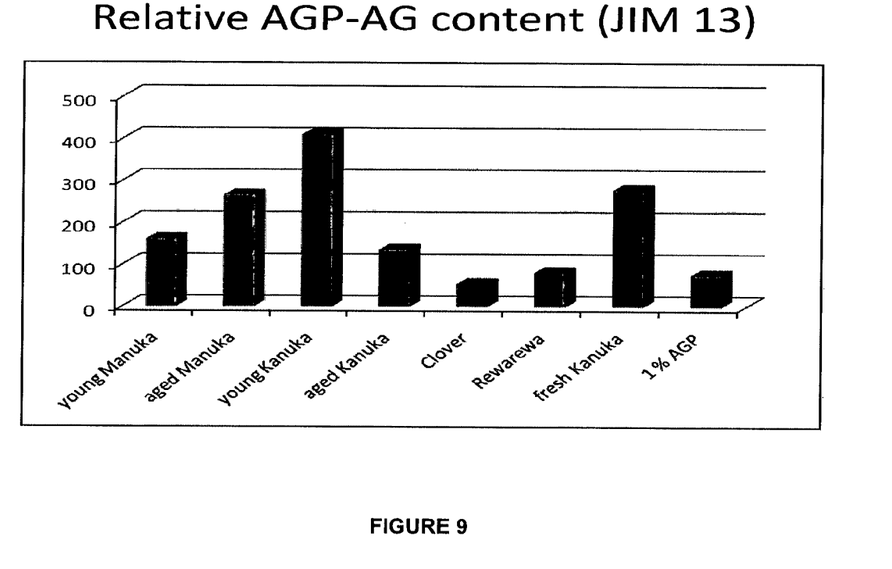
FIG. 9 illustrates the relative amount of AGP content of various honeys tested via the AGP-ELISA protocol established for this invention.

As shown in FIG. 9, two manuka, three kanuka, one clover and a rewarewa honey were tested for their AGP content with the AGP-ELISA protocol above. The colour change in the reaction wells was measured at 405 nm and relative changes used to quantify the amount of AGP in the samples. The results show that there are considerable differences in relative concentrations of AGP between different honeys. It is readily observable that young kanuka honey has more than eight times the amount of AGP antigens then the test clover honey. The honey AGP-ELISA protocol established for this invention has been found to be a useful tool to select honeys for their AGP content. Note that the above results shown in FIG. 9 do not include the ultrafiltration of honey samples to remove the sub 5 kDa fractions.

Example 10

The apisimin content in various sample materials was tested utilising the Apisimin-ELISA protocol established for this invention as follows:

To detect apisimin a microtiterplate was incubated overnight with sample material. The plate was washed and blocked with Bovine Serum Albumin. A monoclonal antibody against apisimin (developed for and owned by Comvita New Zealand Limited) was incubated in the plate for 1 hour and after washing a secondary antibody was administered. The HRP labelled secondary antibody was detected with TMB. The resulting colour change was measured at 450 nm.

Aspects of the AGP and apisimin compositions, methods and uses have been described by way of example only and it should be appreciated that modifications and additions may be made thereto without departing from the scope of the claims herein.

What we claim is:

1. An immunostimulatory composition comprising a therapeutically effective amount of:
    a) honey derived AGP; and
    b) an isolated and/or purified apisimin protein comprising the sequence set forth in SEQ ID NO. 1 and/or one or more peptides with at least 95% homology thereto,
    wherein the concentration of honey derived AGP in the immunostimulatory composition is greater than approximately 1 μg/ml, the concentration of apisimin proteins or peptides in the immunostimulatory composition is greater than approximately 5 μg/ml, and wherein the combination of the AGP and apisimin protein and/or the one or more peptides stimulates an immune response.

2. The immunostimulatory composition as claimed in claim 1 wherein the honey derived AGP is in a form selected from the group consisting of: honey with naturally derived AGP; AGP isolated and/or purified from honey; an AGP containing honey fraction; an AGP containing honey isolate; an AGP containing honey analogue; and combinations thereof.

3. The immunostimulatory composition as claimed in claim 1 wherein the apisimin proteins or peptides are isolated from royal jelly.

4. The immunostimulatory composition as claimed in claim 1 wherein the apisimin proteins or peptides are produced via recombinant methods.

5. The immunostimulatory composition as claimed in claim 1 wherein the apisimin proteins or peptides are produced via chemical synthesis.

6. The immunostimulatory composition as claimed in claim 1 wherein the concentration of AGP in the honey derived AGP is from 1 to 20 µg/ml.

7. The immunostimulatory composition as claimed in claim 1 wherein the honey derived AGP is type II arabinogalactan protein.

8. The immunostimulatory composition as claimed in claim 1 wherein the concentration of apisimin proteins or peptides is from 5 to 50 µg/ml.

9. The immunostimulatory composition as claimed in claim 1 wherein the immunostimulatory composition is formulated for oral or topical delivery.

10. The immunostimulatory composition as claimed in claim 1 wherein the honey derived AGP is obtained from a plant genus selected from the group consisting of *Leptospermum, Kunzea, Weinmannia, Knightia, Metrosideros, Fagus, Trifolium, Myrtaceae*, and combinations thereof.

11. The immunostimulatory composition as claimed in claim 1 wherein the honey derived AGP is obtained from honey selected from the group consisting of kanuka floral origin honeys, kanuka nectars, manuka floral origin honeys and manuka nectars.

12. A method of manufacturing an immunostimulatory composition comprising the steps of:
   a) testing the concentration of AGP in a selection of honeys, honey fractions, or honey isolates batch samples;
   b) testing the concentration of apisimin protein comprising the sequence set forth in SEQ ID NO. 1 and/or one or more peptides with at least 95% homology thereto, in the selection of honeys, honey fractions, or honey isolates batch samples; and
   c) selecting and blending the batch samples to prepare the immunostimulatory composition;
   wherein the concentration of AGP in the immunostimulatory composition is greater than approximately 1 µg/ml, the concentration of apisimin proteins or peptides in the immunostimulatory composition is greater than approximately 5 µg/ml, and wherein the combination of the AGP and apisimin protein and/or the one or more peptides stimulates an immune response.

13. The method as claimed in claim 12 wherein the AGP and apisimin concentrations are tested via Enzyme Linked Immuno Sorbent Assay (ELISA) analysis.

14. The method as claimed in claim 13 wherein the honeys, honey fractions, or honey isolates are ultrafiltered to obtain a high molecular weight fraction wherein components approximately less than or equal to 5 kDa are removed.

15. The method as claimed in claim 12, further comprising the steps of:
   d) adding apisimin protein comprising the sequence set forth in SEQ ID NO. 1 and/or one or more peptides with at least 95% homology thereto, isolated from royal jelly or produced via recombinant methods; and/or
   e) adding additional AGP.

16. The method as claimed in claim 12 wherein the immunostimulatory composition is filtered using a 5 to 30 kDa pore size filter to obtain a high molecular weight fraction.

\* \* \* \* \*